United States Patent [19]
Vergnolle et al.

[11] Patent Number: 5,298,188
[45] Date of Patent: Mar. 29, 1994

[54] FLUORINATED LIQUID CRYSTALS

[75] Inventors: Marie Vergnolle, Palaiseau; Francoise Soyer, Villebon Sur Yvette; Pierre Le Barny, Orsay; Jean-Claude Dudois, St. Remy Les Chevreuse, all of France

[73] Assignee: Thomson-CSF, Puteaux, France

[21] Appl. No.: 840,311

[22] Filed: Feb. 24, 1992

[30] Foreign Application Priority Data

Feb. 26, 1991 [FR] France ................... 91-02257

[51] Int. Cl.$^5$ .............. C09K 19/30; C09K 19/12; C07C 41/00; C07C 22/00
[52] U.S. Cl. .................. 252/299.63; 252/299.66; 568/631; 568/647; 570/144
[58] Field of Search .............. 252/299.63, 299.66; 568/631, 647

[56] References Cited

U.S. PATENT DOCUMENTS

| 4,798,680 | 1/1989 | Nohira et al. | 252/299.01 |
| 4,867,903 | 9/1989 | Nohira et al. | 252/299.61 |
| 4,873,018 | 10/1989 | Nohira et al. | 252/299.01 |
| 4,917,821 | 4/1990 | Mori et al. | 252/299.63 |
| 5,051,506 | 9/1991 | Wand et al. | 544/298 |
| 5,139,697 | 8/1992 | Togano et al. | 252/299.61 |

FOREIGN PATENT DOCUMENTS

| 0267585 | 5/1988 | European Pat. Off. |
| 0294852 | 12/1988 | European Pat. Off. |
| 0326086 | 8/1989 | European Pat. Off. |
| 0343487 | 11/1989 | European Pat. Off. |
| 0350893 | 1/1990 | European Pat. Off. |
| 0350936 | 1/1990 | European Pat. Off. |
| 2043282 | 2/1990 | Japan |

Primary Examiner—Robert L. Stoll
Assistant Examiner—C. Harris
Attorney, Agent, or Firm—Oblon, Spivak, McClelland, Maier & Neustadt

[57] ABSTRACT

The disclosure relates to fluorinated chiral liquid crystals that incorporate a cyclohexyl grouping in their structure. They can be used as dopants and lead to mixtures of ferroelectric liquid crystals that have an application in display systems. They meet the following chemical formula.

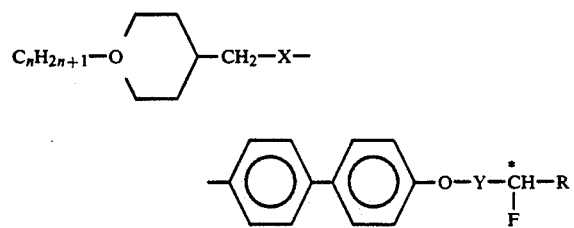

with $1 \leq n \leq 14$
if $X = CH_2$  $Y = -CH_2-$ with $R = C_mH_{2m+1}$ and $5 \leq m \leq 16$

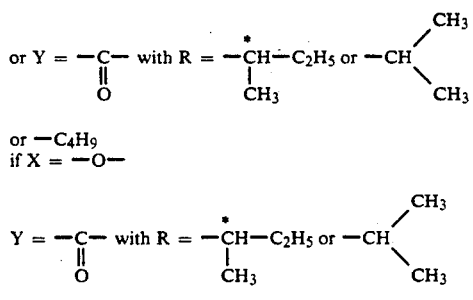

6 Claims, 3 Drawing Sheets

FLUORINATED LIQUID CRYSTALS

BACKGROUND OF THE INVENTION

1. Field of the Invention

An object of the present invention is fluorinated chiral liquid crystals that incorporate a cyclohexyl grouping in their structure, can be used as dopants and lead to mixtures of ferroelectric liquid crystals that have an application in display systems.

At present, only nematic liquid crystals have found application in the field of display systems. This has led chiefly to display units using the nematic helix mode and, more recently, to super-twisted nematic (STN) display units.

2. Description of the Prior Art

The drawback of display units of this type is their poor angle of view and their high response time which is of the order of about ten milliseconds. This limits their scope for development.

The invention of a display system based on the use of ferroelectric liquid crystals by N. A. Clark and S. Lagerwall (Applied Physics Letter, Vol. 36, No. 89, 1980) in 1980 has led to a new electrooptical effect induced by linear coupling between the permanent electrical polarization of the molecules and the electrical addressing field having switching times that are smaller than those of standard nematic helix displays by three orders of magnitude.

For reasons of symmetry, the ferroelectricity of the $S^*_C$ phase can be observed only if the helical structure is uncoiled. This condition is achieved in the display system proposed by Clark and Lagerwell when the $S^*_C$ phase is introduced into a cell with a thickness of less than 2 $\mu$m.

The electrooptical performance characteristics of display units such as these depend greatly on the mesomorphic material used.

In an initial approximation, the response time $\tau$ of a mixture $S^*_C$ is given by the following relationship:

$$\tau = \frac{\eta}{P_S \times E}$$

where $\eta$ represents the rotational viscosity of the liquid crystal, $P_S$ its spontaneous polarization and E the applied electrical field.

The mixtures $S^*_C$ should have a certain number of properties such as:
being thermally and photochemically stable;
getting aligned easily;
displaying the following phase succession:

$S^*_C, S_A, N^*, L$ possessing a wide range of mesomorphic temperature having an angle of tilt close to 22.5°.

To obtain an $S^*_C$ mixture that fulfils all these conditions, it is preferred at present to dope an $S_C$ mixture with one or more dopants.

The $S_C$ mixture contributes:
the succession of the phases
the domain of existence in temperature of these phases,
low viscosity,
dielectric anisotropy and birefringence.

The chiral dopants contribute the chirality and the polarization. The dopant should furthermore not modify the transition temperatures of the $S_C$ matrix and should not increase the viscosity of the final mixture.

Finally, in order to meet these conditions, the present invention proposes a new formula of fluorinated liquid crystals incorporating a cyclohexyl grouping in their structure, usable as a dopant of an $S_C$ matrix.

SUMMARY OF THE INVENTION

An object of the invention, therefore, is a family of fluorinated chiral liquid crystals incorporating a cyclohexyl grouping in their structure, wherein said family meets the following general formula:

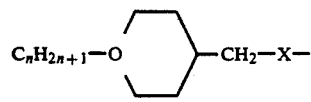

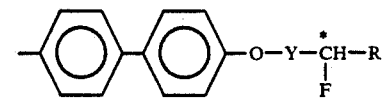

with $1 \leq n \leq 14$
if $X = CH_2$ $Y = -CH_2-$ with $R = C_mH_{2m+1}$ and $5 \leq m \leq 16$

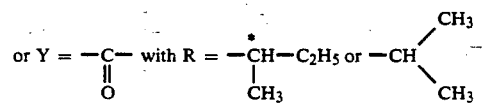

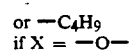
if $X = -O-$

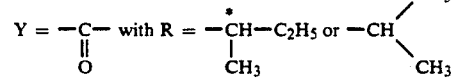

or $-C_4H_9$

This family has the following advantages:
the presence of three cycles in the chemical structure of the molecules of the formula leads to the existence of mesomorphs on a wide range of temperature;
the C—F bond which provides the greatest contribution to the polarization of the mixture leads to derivatives that are more stable than similar chlorinated derivatives;
finally, the use of a trans ethyl cyclohexane or cyclohexylethoxy radical plays a part in the obtaining of mixtures with low viscosity as compared with the corresponding benzoic derivatives.

BRIEF DESCRIPTION OF THE DRAWINGS

The invention shall be understood more clearly from the following description and from the appended drawings, of which.

Synthesis of the Compounds

Synthesis of 4-[trans-(4 alkyl cyclohexane) methoxy] 4' (2 fluoro alkyl 1-methoxy) biphenyl. (Compound I according to the prior art)

Figure 1:
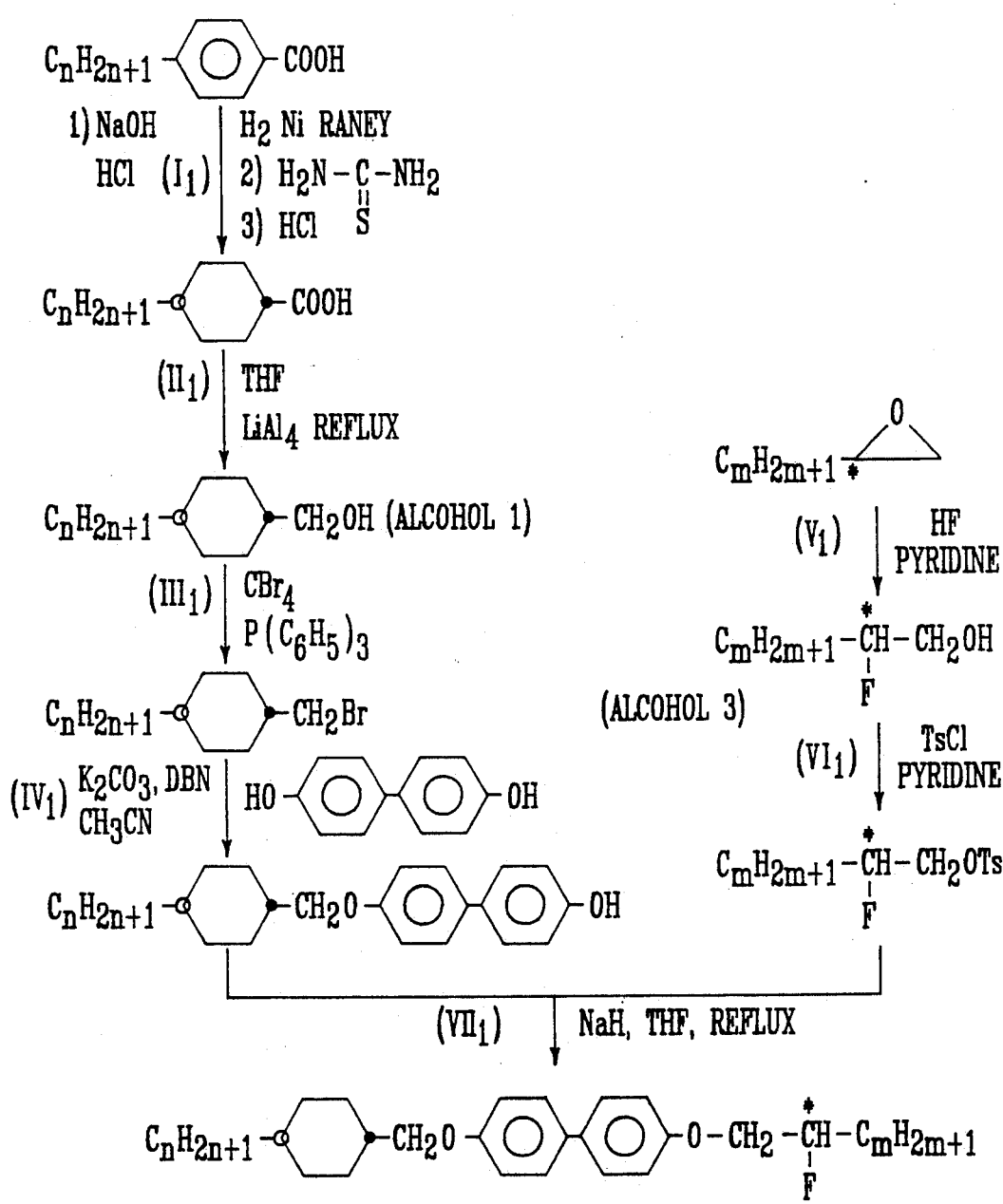
FIG. 1 shows the diagram of the synthesis of a first example of a molecule according to the prior art.

These compounds are synthesized in 7 steps starting with 4 alkylbenzoic acid and the corresponding chiral epoxide according to the reaction diagram described in FIG. 1. 4 pentyl cyclohexyl acid is commercially available. The hydrogenation of the benzenic core of 4 alkylbenzoic acid and the separation of the cis and trans isomers by means of an inclusion compound with thiourea entails no problems for those skilled in the art. Hereinafter, the most difficult steps shall be described in greater detail.

The structure of the products obtained was established by NMR $^1$H on VARIAN T 60 (and T 80) and BRUKER AM 250 and WPSY 80 spectrometers in using tetramethylsilane (TMS) as an internal reference and deuterized chloroform (CDCl$_3$) as a solvent. The mass spectra were made on a NERMAG R 10 10 C quadrupole spectrometer with chemical ionization (reacting gas NH$_3$) and by electron impact. The rotatory power values $a_D{}^3$ were measured with sodium yellow line on a Perkin-Elmer polarimeter (benzene as solvent).

Synthesis of trans-(4-pentylcyclohexane) methanol corresponding to the second step of FIG. 1

In a Woulff bottle and, under argon, trans-4-pentylcyclohexanoic acid (10 g namely 50.5 mmoles) in 40 ml of dry tetrahydrofuranne (THF) is added drop by drop to a solution of LiAlH$_4$ (2.85 g namely 75.8 mmoles) in 60 ml of THF at 0° C. $^4$When the addition is over, the mixture is refluxed for one hour.

Then the mixture is cooled to 0° C. and then 150 ml of H$_2$O and finally 20 ml of HCL 2N are added. The aqueous phase is then extracted through twice 100 ml of ether, the organic phases are brought together and drying and filtering operations are carried out and the solvent is dry-evaporated. Then 7.9 g of a colorless oil are obtained.

Synthesis of trans-(4-pentylcyclohexane) bromomethane (step III$_1$)

Tetrabromomethane (18.7 g namely 56.5 mmoles) and the above alcohol are dissolved in 50 ml of dry methylene chloride.

Solid triphenylphosphine (14.7 g namely 56.5 mmoles) is then added by fractions. A yellow color appears along with a heating phenomenon. Then 200 ml of a 1/1 solution of ether and petroleum ether are added. The white precipitate obtained is filtered and the mother liquor is evaporated. The NMR spectrum analysis of the crude product at 60 MHZ shows that triphenylphosphine oxide remains. This triphenylphosphine oxide is purified on silica, using heptane as an elutant. 9.8 g of a colorless oil are then obtained.

Synthesis of 2 (+) fluoro octane -1-ol corresponds to the fifth step (V$_1$)

30 ml of hydrofluoric acid (HF)/pyridine are cooled in a polyethylene beaker under argon. Epoxide (8.4 g namely 65 mmoles) in 20 ml of ether is then added drop by drop. The mixture is left to shake for two hours at ambient temperature. 100 ml of water are added and then the reaction medium is neutralized by a solution of soda 5N. 8.4 g of a slightly yellow oil is obtained, and this oil crystallizes. The crude product is purified by high pressure liquid chromatography (HPLC) on silica. Two fractions possessing a non-zero $a_D$ are isolated.

The following are the measurements:

fraction a $a_D = -8.9°$.

fraction b $a_D = -12.5°$ ($a = -13.1°$ according to the literature)

the fraction b corresponds to the chiral alcohol expected (alcohol 3).

Synthesis of 2(-) fluoro-1-octane (4-methyl phenyl solfonyl) 4 corresponding to the 6th step (VI$_1$)

Tosyl chloride (2 g namely 10.5 mmoles) in 100 ml of chloroform is added drop by drop to at 0° C. to a solution of alcohol 3 (1.1 g namely 7.6 mmoles) and pyridine (1.4 g namely 17.3 mmoles) in 20 ml of chloroform (CHCl$_3$). The mixture is left for two hours at ambient temperature and the development of the reaction is checked by thin layer chromatography. Fluorinated alcohol remains. 0.4 equivalent of pyridine and tosyl is added. The mixture is left at ambient temperature for 24 hours. 30 ml of water and 30 ml of ether are added. The product is washed with 10 ml of HCL 2N, neutralized by twice 10 ml of a saturated solution of NaHCO$_3$, and then washed with 10 ml of water. The organic phase is extracted and then dried on MgSO$_4$. The product is filtered and concentrated. After purification by HPLC on silica, 1.66 of a slightly yellow oil is recovered.

Synthesis of 4-trans-(4-pentylcyclohexane) methoxy, 4'hydroxybiphenyl 5 (step IV$_1$)

Dihydroxy-4, 4'biphenyl (10 g namely 53.7 mmoles) and potassium carbonate (28.6 g namely 0.27 mmoles) in 400 ml of acetonitrile are refluxed for one hour. The mixture is brought back to ambient temperature and then the brominated derivative in 30 ml of acetonitrile is added. Refluxing is done. After 24 hours, there is little product formed. Then 100 ml of toluene are added and the mixture is again taken to 80° C. for 24 hours. Tracking by thin layer chromatography shows that there is no change. Then 3 times 3 ml of 1.5 - diazobicyclo (3-4-0) nonene 5 (DBN) is added.

The product is filtered and evaporated. It is re-treated with 300 ml of dichloromethane, washed with 40 ml of sulphuric acid 1N and then 100 ml of water. The aqueous phases are extracted by two times 50 ml of dichloromethane. The organic phases are brought together, they are dried on MgSO$_4$, then filtered and then concentrated. 1.8 g of crude product are recovered. It is purified by filtration on silica.

Synthesis of 4-[trans-(4 pentylcyclohexane) methoxy], 4'(2 fluoro heptane 1 - methoxy) biphenyl 6 (step VII$_1$)

A 100 ml Woulff bottle is dried by a flame under argon. Sodium hydride is washed with 10 ml of pentane, again under argon. Then it is re-treated with 20 ml of dry THF and mono-etherized phenol 5 (1 g namely 2.8 mmoles) in 40 ml of THF is added drop by drop. Refluxing is done for one hour. The product is returned to ambient temperature and tosyl derivative (0.86 g namely 2.8 mmoles) in 20 ml of THF is added. Refluxing is done for five hours, there being no change in the reaction. Hydrolysis is carried out with 50 ml of $NH_4Cl$ and then washing is done with 50 ml of water while the pH is checked. The aqueous phases are extracted with three times 20 ml of ether, the product is dried on $MgSO_4$. Operations of filtering and concentration are carried out. 1.4 g of crude product are then recovered.

After purification with HPLC, 510 g of a white solid are recovered.

Figure 2:
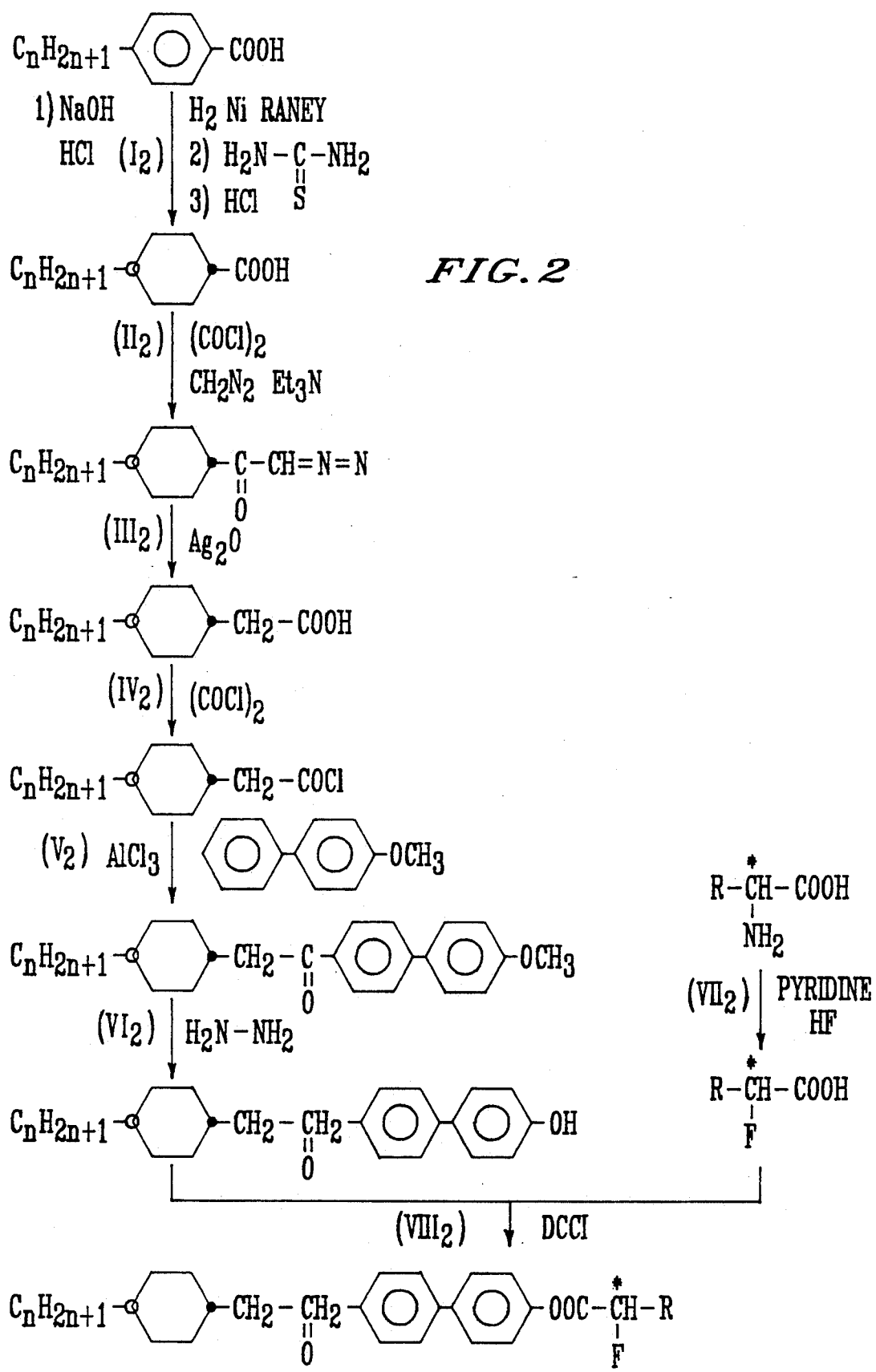
FIG. 2 shows the diagram of the synthesis of an example of a molecule according to the invention.

Synthesis of 4-[trans-(4 alkyl cyclohexyl) ethyl 4' (2 fluoro alkanoyloxy] biphenyl, the reaction diagram of which is shown in FIG. 2 (compound II according to the invention)

These compounds are synthesized in eight steps starting with 4 alkylbenzoic acid and the corresponding amino acid (leucin, isoleucin, valine) (FIG. 2).

The synthesis of 4 hydroxy 4' alkyltrans cyclohexylethyl biphenyl is described in the patent No. 89 12026 filed by the Applicant.

The synthesis of 2 fluoro 3 methyl pentanoic acid has beein done according to a procedure described by R. Buchecker, S. M. Kelly and J. Fuenfschilling (Liq. Cryst. 8 (2) 217–227 (1990).

Synthesis of 2 fluoro 3 methyl pentanoic acid (step $VII_2$)

5.24 g (0.04 mole) of isoleucin and then 100 ml of HF pyridine 70% are introduced into a teflon beaker.

The mixture is cooled to 15° and 44 ml of distilled pyridine are added in little quantities. The formation of white fumes is observed.

The mixture is cooled to 0° C. and 4.1 g (0.06 mole) of sodium nitrite is added. The mixture is stirred and allowed to return to ambient temperature, then the stirring is continued for five days.

The solution is poured into a mixture of 400 ml of water and 400 g of ice.

Extraction is done under ether.

The crude product (about 2 g) is purified by distillation under vacuum $E_7 = 80°$ C.

400 mg of acid is obtained.

Yield $\rho = 7.5\%$.

Synthesis of 4-trans-(4 heptyl cyclohexyl ethyl 4' (2 fluoro 3 methyl pentanoyloxy) biphenyl (step $VIII_2$)

0.23 g (0.6 mmole) of 4-trans-4 (heptyl cyclohexyl) ethyl 4' hydroxy biphenyl, 0.4 g (3 mmole) of 2 fluoro 3 methyl pentanoic acid, 5 ml of methylene chloride, 0.74 g (3.6 mmole) of dicyclohexylcarbodiimide DCCI and 0.148 g (1 mmole of piperidinopyridine are introduced into an erlenmeyer flask. The mixture is shaken under ambient temperature for 36 hours.

The urea precipitate is eliminated by filtration. The filtrate is dry evaporated.

The crude product is purified by chromatography on $SiO_2$ (hexane 60 - toluene 40 as the elutant) followed by a recrystallization in hexane. 0.18 g of product is obtained.

Yield 60%.

Properties of the synthesized bodies

The compounds according to the invention have been studied by differential enthalpic analysis and by optical microscopy. The results are brought together in table No. 1.

TABLE 1

| Index | n | x | R | Y | mesomorphic properties |
|---|---|---|---|---|---|
| (I) | 5 | O | $C_6H_{13}-$ | $-O-$ | $S_385,2\ S_B145\ S_A175,5L$ |
| (II) | 7 | $-CH_2-$ | $C_2H_5-\underset{\underset{CH_3}{\mid}}{CH}-$ | $-COO-$ | C 56,5 S 137 L |

The compound (I) does not get crystallized.

The phases $S_3$ and S are highly ordered smectic phases.

The compounds (I) and (II) were introduced as dopants into a mixture M displaying an $S_C$ phase (Merck mixture referenced ZLI3234B) and possessing the following succession of phases:

$S_C76S_A80N96L$

The following properties were measured:
transition temperatures of the final mixture,
polarization as a function of the temperature,
angle of tilt as a function of the temperature,
measurement of the response time.

To obtain a homogeneous mixture after incorporation of the dopant, the following procedure was carried out. After the weighing of the dopant and of the mixture M in one and the same receptacle, a homogeneous solution was made by the addition of a purified solvent with a low boiling point ($CH_2Cl_2$ or $CHCl_3$). This solution was then filtered on a 1 μm Millipore filter in a environment rid of dust. Finally, the solvent was eliminated by slow evaporation under a nitrogen stream at 40° C., then under vacuum.

All the dopants according to the invention are soluble to a concentration of 10% by weight in the mixture.

The transition temperatures of the doped mixtures (doped at a rate of 10% by weight of dopant in the final mixture obtained) were determined by differential enthalpic analysis and by optical microscopy. The results are brought together in table 2.

TABLE 2

| dopant | $S_C^*$ | | $S_A$ | | $N^*$ | | L |
|---|---|---|---|---|---|---|---|
| (I) | • | 71,5 | • | 85,5 | • | 103 | • |
| (II) | • | 68,8 | • | 87,8 | • | 98,5 | • |

The measurement of polarization, response time and tilt angle require the making of measurement cells. The cells are made out of rectangular (2×3 cm) glass plates with a thickness of 1 mm, covered with non-annealed ITO (indium tin oxide). The cells are manufactured in five steps.

A conductive strip with a width of 1 cm is first of all defined on each glass plate.

Then, these strips are coated with a film of polyvinyl alcohol (Rhodoviol 4.125) by spin coat deposition of a 3% aqueous solution. After drying at 100° C. for one hour, the PVA film is subjected to friction by means of a friction machine (for example of the Asulab brand) in order to induce an non-degenerated planar orientation. The cells are then sealed in by means of an araldite glue. The contacts between an electrical wire and a strip are made by means of silver bonder spots. Finally, the material is introduced by capillarity.

The polarization was measured by using a triangular signal. The excitation field used had a value of 15V/μm. The measurements were made at 100 Hz.

Figure 3:
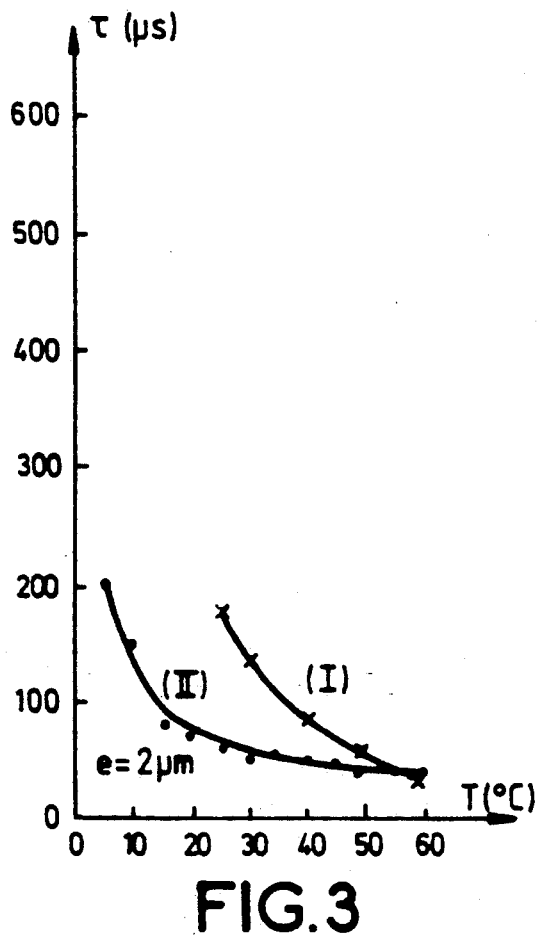
FIG. 3 shows changes in the spontaneous polarization (with the temperature) of mixtures obtained with the compound (I) and (II)

FIG. 3 shows the spontaneous polarization obtained with the compounds (I) and (II).

The tilt angle is measured by using an electrooptical method. A DC field (+E) is applied to the terminals of the cell which is observed under the microscope between crossed polarizer and analyzer. The dipoles get aligned in the direction of the field and the extinguishing position is determined. Then, the direction of the field is reversed (−E), and this reverses the direction of the dipoles. The molecules are then rotated by an angle of 2Φ. The sample has to be rotated by an angle of 2Φ to recover an extinguishing position The direction in which the sample has to be rotated to recover an extinguishing position also gives the sign of the polarization. The electrical field applied has a value of 15 V/μm.

Figure 4:
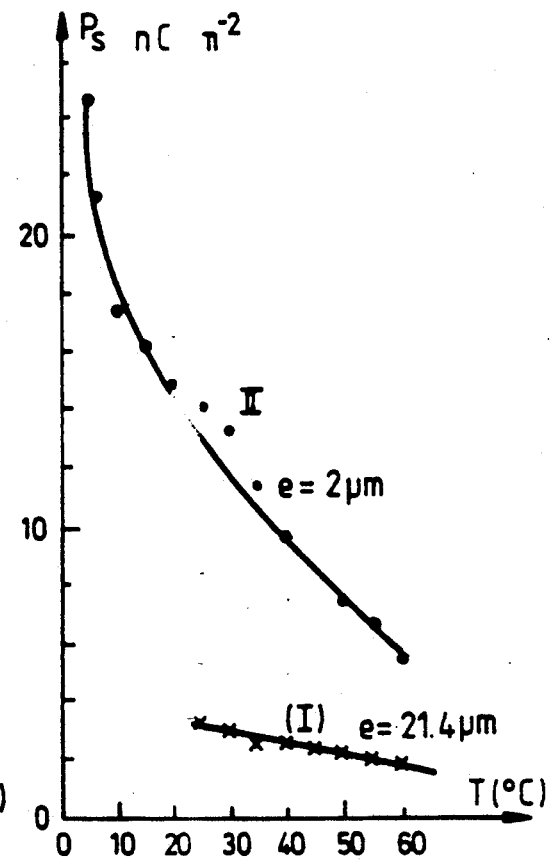
FIG. 4 shows the changes in the angle of tilt as a function of the temperature for mixtures obtained with the compounds (I) and (II)

FIG. 4 shows the angle of tilt as a function of the temperature of the mixtures obtained with the compounds (I) and (II).

The electrooptical response time of the materials was measured by applying a voltage in the form of square waves to the terminals of a measurement cell, corresponding to an electrical field of 15 V/μm.

Figure 5:
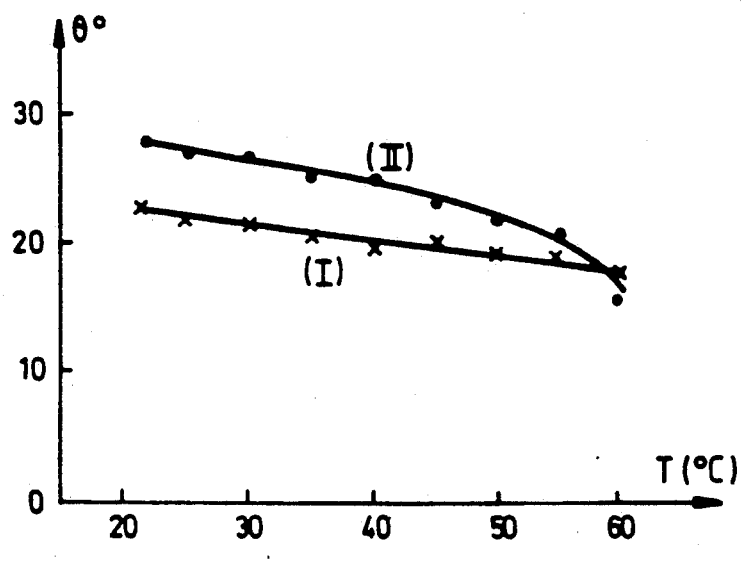
FIG. 5 shows changes in the electrooptic response time with the temperature for mixtures obtained with the compounds (I) and (II).

FIG. 5 shows the changes of the response time τ as a function of the temperature for mixtures obtained with the compounds (I) and (II).

What is claimed is:

1. A liquid crystal chiral compound of the formula

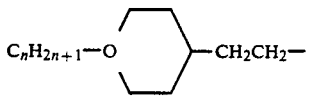
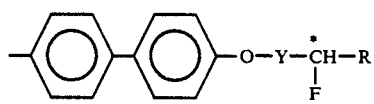

wherein
$1 \leq n \leq 14$
Y is —CH$_2$— or

with the proviso that when Y is —CH$_2$— R is C$_m$H$_{2m+1}$ and
$5 \leq m \leq 16$,
when Y is

R is

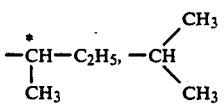

or —C$_4$H$_9$.

2. The liquid crystal chiral compound according to claim 1, wherein Y is —CH$_2$—.

3. The liquid crystal chiral compound according to claim 1, wherein Y is

4. The liquid crystal chiral compound according to claim 3, wherein R is

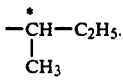

5. The liquid crystal chiral compound according to claim 3, wherein R is

6. The liquid crystal chiral compound according to claim 3, wherein R is C$_4$H$_9$.

UNITED STATES PATENT AND TRADEMARK OFFICE
CERTIFICATE OF CORRECTION

PATENT NO. : 5,298,188
DATED : March 29, 1994
INVENTOR(S) : Marie VERGNOLLE, et al.

It is certified that error appears in the above-indentified patent and that said Letters Patent is hereby corrected as shown below:

```
On the title page, Item [75], the 4th inventor's last name should
   read as follows:

--Dubois--
```

Signed and Sealed this

Eighteenth Day of October, 1994

Attest:

BRUCE LEHMAN

*Attesting Officer*  *Commissioner of Patents and Trademarks*